US006297427B1

(12) United States Patent
Yeh et al.

(10) Patent No.: US 6,297,427 B1
(45) Date of Patent: Oct. 2, 2001

(54) INSECT RESISTANT USE OF SWEET POTATO SPORAMIN GENE AND METHOD FOR CONTROLLING PESTS USING THE GENE

(75) Inventors: Kai-Wun Yeh; Mei-In Lin; Shu-Jen Tuan; Yih-Ming Chen; Chu-Yung Lin; Suey-Sheng Kao, all of Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/038,542

(22) Filed: Mar. 11, 1998

(30) Foreign Application Priority Data

Mar. 11, 1997 (TW) .................................. 86103072

(51) Int. Cl.[7] .......................... C12N 15/82; C12N 15/70; C12N 1/21; C07H 21/04
(52) U.S. Cl. .................... 800/279; 536/23.6; 435/252.3; 435/320.1; 800/294
(58) Field of Search ................................... 800/279, 302, 800/301; 536/23.6; 435/320.1, 252.3, 419, 468, 469

(56) References Cited

U.S. PATENT DOCUMENTS 5,306,863 * 4/1994 Hilder et al. .......................... 800/205

FOREIGN PATENT DOCUMENTS 0 135343 3/1985 (EP).

OTHER PUBLICATIONS

Matsuoka, K. and K Nakamura, Propepetide of a precursor to a plant vacuolar protein required for vacuolar targeting PNAS, USA 88:834–838, 1991.*

Yeh, K. et al, Functional activity of sporamin from sweet potato (Ipomoea batatas Lam.): a tuber storage protein with trypsin inhibitory activity. Plant Mol Biol 33:565–570, Feb. 1997.*

Hattori, T. et al, Structural relationship among the members of a multigene family coding for the sweet potato tuberous protein. Plant Mol Biol 13:561–572, 1989.*

GenBank listing of Accession No. X15091, "Sweet potato mRNA for sporamin A tuberous root storage protein (clone pIM044)" Sep. 12, 1993.

Yeh, et al., (1997) *Plant Cell Rep.*, vol. 16, No. 10, pp. 696–699.

Yeh et al., (1994) *EMBL Sequence Database Accession* No. U17333.

Yeh et al., (1997) *Plant Mol. Biol.*, vol. 33, No. 3, pp. 565–570.

Wang et al., (1996) *Taiwania*, vol. 41, No. 1, pp. 27–34.

Rayn, C.A., (1990) *Annual Review of Phytopathology*, vol. 28, pp. 425–449.

Database WPI, Section Ch, Week 9119, Derwent Publication Ltd., Class D16, AN 91–136273 & JP 03072826 (Abstract).

Database WPI, Section Ch, Week 8645, Derwent Publication Ltd., Class B04, AN 86–29614 & JP 61219388 (Abstract).

Lin, Mei–In, (Oct. 1996) *Study on Gene Expression and Insect–Resistance of Sweet Potato Sporamin in Transgenic Tobacco*, Master Thesis (Abstract) National Tiawan University.

* cited by examiner

Primary Examiner—Gary Benzion
Assistant Examiner—David H Kruse
(74) Attorney, Agent, or Firm—McDonnell Boehnen Hulbert & Berghoff

(57) ABSTRACT

The present invention provides for the use of a sweet potato sporamin gene in insect-resistance, in which the gene is inserted into an appropriate vector, then the gene is transformed into plants to enhance the plant's insect resistance, for the purpose of controlling pests.

10 Claims, 5 Drawing Sheets

```
1   AATTAAACAT CATTACCCTC TCGCTTTCTC CCAATTAAGG TTGTCATCTG
51  CCACCATGAA AGCCCTCACA CTGGCACTCT TCTTAGCCCT TTCCCTCTAT
101 CTCCTCCCCA ATCCCGCCCA TTCCAGGTTC AATCCCATCC GCCTCCCCAC
151 CACACACGAA CCCGCCTCCT CTGAAACTCC AGTACTGGAC ATCAACGGCG
201 ACGAGGTCCG CGCCGGGGGG AACTACTACA TGGTCTCCGC CATATGGGGA
251 GCCGGCGGGG GAGGGCTAAG ACTCGCCCAC TGGACATGA TGTCCAAATG
301 CGCCAGCGAC GTCATCGTAT CCCCCAACGA CTTAGACAAC GGCGACCCCA
351 TCACCATCAC GCCGGGCACG GCCGACCCGG AATCCACCGT GGTCATGGCG
401 TCGACGTACC AGACTTTCCG GTTCAACATC GCCACCAACA AGCTCTGCGT
451 GAACAACGTG AACTGGGGAA TCCAGCACGA CAGCGCGTCC GGGCAGTATT
501 TCCTGAAAGC CGGCGAGTTT GTGTCCGACA ATAGCAACCA GTTCAAGATT
551 GAGCTGGTGG ATGCCAACCT TAACTCCTAC AAACTCACTT ACTGTCAGTT
601 CGGCTCCGAT AAATGCTACA ACGTCGGCAG ATTCCACGAC CACATGTTGA
651 GGACCACGCG TTTGGCTCTC TCCAATTCTC CCTTCGTTTT TGTCATCAAA
701 CCTACCGATG TGTAATGTAA CACTGAAAAG CGCCGGTTAT GAGGTTGCAT
751 GGTAGCTATG CAACGTTGCC ACTTTGACAA CGTTGTACGT GTAAGAATAA
801 ACATGCAACA AATCCGAGCT CGTATGGTTG TGTAAATCCT AATAAATCC
851 GAAGAAATAA TAAGGATAAA ATATTATCCT GTGTTTGTTT TAATTCTCC
```

TIA— • • • • • • • • • • •

INSECT RESISTANT USE OF SWEET POTATO SPORAMIN GENE AND METHOD FOR CONTROLLING PESTS USING THE GENE

FIELD OF THE INVENTION

The present invention provides the insect resistant use of sweet potato sporamin gene, and a method for controlling pests using the gene.

BACKGROUND OF THE INVENTION

In the past few years, according to the development of genetic engineering techniques, the introduction of genes encoding insect-resistant substances into plants by genetic techniques can enhance the insect-resistance of the transgenic plants. The insect-resistant substances include the toxic crystalline protein, protease inhibitor and the like produced by *Bacillus thuringiensis*.

Sporamin is a storage protein enriched in the tuberous roots of sweet potato, which was first purified by Maeshima et al. (Maeshima et al., "Characterization of major proteins in sweet potato tuberous roots." *Phytochemistry*, Vol. 124. pp. 1899–1902, 1985). The amount of Sporamin is about 60% to 80% of the total soluble proteins of sweet potato. Sporamin is present most in tuberous roots, little in other tissues and organs (Hattori et al., "High-level expression of tuberous root storage protein genes from sweet potato in stems of plantlets grown in vitro on sucrose medium." *Plant Mol. Biol.* Vol. 14, pp. 595–604, 1990). In 1989, Hattori et al. isolated the sporamin gene from the cDNA library of tuberous roots of sweet potato (Hattori et al., "Structural relationship among the members of multigene family coding for the sweet potato tuberous roots storage proteins." *Plant Mol. Biol.* Vol. 13, pp. 563–572, 1989).

Besides the function of storing nitrogen source, the amino acid sequence of sporamin predicted from the cDNA thereof has been found to have certain homology to Kunitz type trypsin inhibitors of Leguminosae plants (Hattori et al., "Sucrose-induced expression of genes coding for the tuberous root storage protein sweet potato in leaves and petioles." *Plant Cell Physiol.* Vol. 32, pp. 79–86, 1991). However, Hattori et al. suggested that sporamin has no trypsin inhibitor activities (Hattori et al., 1989).

Moreover, with regard to the relationship between sweet potato sporamin gene and trypsin inhibitor activities was discussed by Chen, Jen-chin in "The research in the genome of sweet potato," Dept. of Botany, National Taiwan University, Master thesis. pp. 1–122 (1994). It is suggested in the article that sporamin might possess trypsin inhibitor activity.

The purpose of the present invention is to find appropriate genes which can be transformed into plants and provide a method of controlling pests. According to the present invention, it is found that sporamin has insect-resistant ability, so it is possible to use sporamin to control pests.

SUMMARY OF THE INVENTION

The object of the present invention is to provide the use of sweet potato sporamin gene in insect-resistance.

The further object of the present invention is to provide a method for controlling pests, in which the sweet potato sporamin gene is transformed into a plant using the tobacco model to enhance the ability of insect resistance in the plant.

Still the further object of the present invention is to provide a transformation vector, in which the sweet potato sporamin gene is inserted, and then the sweet potato sporamin gene may be transformed into a plant to enhance the ability of insect resistance in that plant.

The present invention also provides a transformed bacterium, which is used as a vehicle to transfer the sweet potato sporamin gene into a plant to enhance the ability of insect resistance in that plant.

BRIEF DESCRIPTION OF THE DRAWINGS

FIG. 1 Full length cDNA sequence of sporamin, in which the translation starting sequence [ATG] and the polyadenylation signal [AATAAA] sequence are underlined (SEQ ID NO:1).

Figure 3:
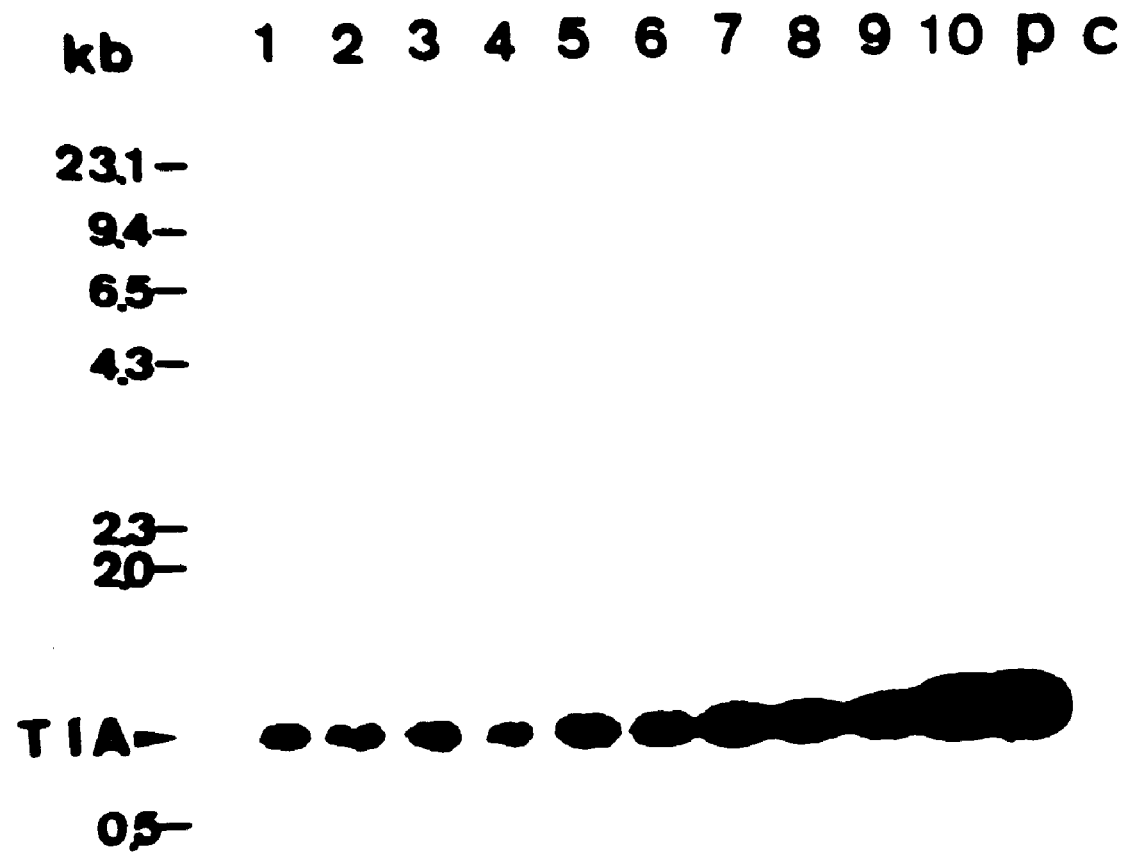

FIG. 3 Northern blotting analysis of transformed *Agrobacterium tumefaciens* using TIA cDNA as gene probe, in which C represents untransformed Agrobacterium LBA 4404 plasmid DNA, P represents vector pBI 121 with sporamin gene insert, and 1–10 represent the plasmid DNA from transformed Agrobacterium.

THE DETAILED DESCRIPTION OF THE INVENTION

The present invention provides a use of sweet potato sporamin gene. As mentioned herein, the sweet potato sporamin gene refers to full length cDNA sequence thereof, as shown in FIG. 1 (SEQ ID NO:1). The cDNA of sporamin gene is 0.93 kb in full length. A preferable example of the present invention is a full length cDNA sequence isolated from sweet potato (*Ipomoea batatas* (L.) Lam Tainong 57) tuberous root, designated spTi-1, which was submitted to GenBank under accession number U17333 (Chen, 1994).

The sweet potato sporamin gene has been proven by the inventor to have trypsin inhibitor activity. Therefore, the possibility of enhancing the ability of insect resistance in the plant and achieving the purpose of controlling pests by transforming that sporamin gene into a plant of tobacco model plants was discussed.

As a vector for inserting the sweet potato sporamin gene, the binary vectors suitable for plant transformation, such as plasmid pBI 121, pBin, pZp and the like are preferable.

The transformation vectors described above are used for transfecting a sporamin gene into plants by utilizing an appropriate bacterium as a vehicle. A preferable example of the present invention is *Agrobacterium tumefaciens* LBA 4404, which is expressed under appropriate control and only contains disarmed Ti plasmid pAL 4404.

The method of controlling pests provided by the present invention is to transform a sporamin gene into a plant, so that the plant may present the property of sporamin, i.e. may exhibit trypsin inhibitor activity, and achieve the purpose of controlling pests. As an embodiment of the present invention is to insert the sporamin gene into an appropriate vector, for transforming the resulting vector into an appropriate bacterium as a vehicle, and coincubate a plant with that bacterium for transducing a sporamin gene into a plant. Thus, the ability of insect resistance in that plant may be enhanced.

Figure 2:
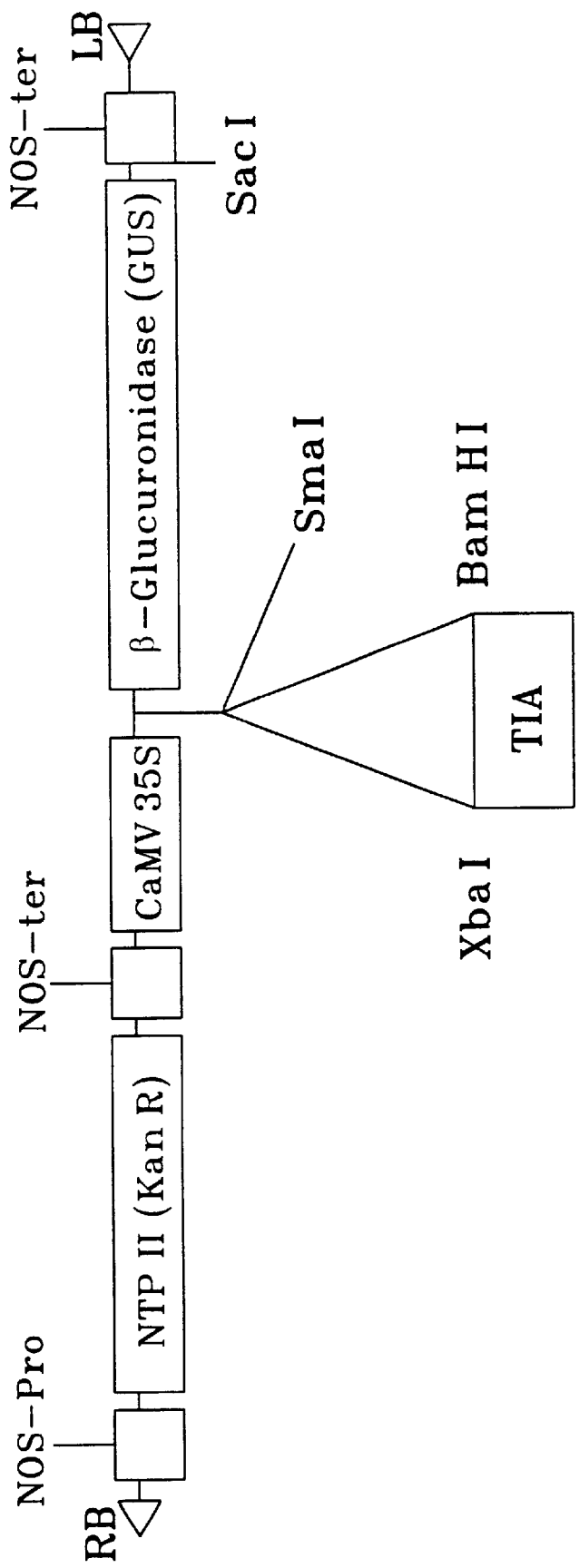
FIG. 2 Plasmid construct of pBI 121, in which the full length cDNA sequence of sporamin was inserted at the XbaI/BamHI site in pBI 121.
Figure 4:
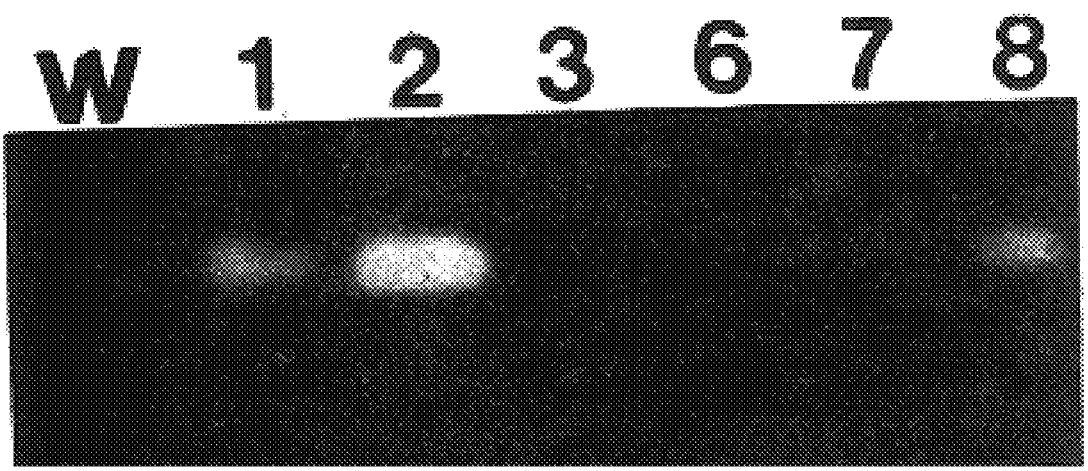
FIG. 4 Analysis of trypsin inhibitor activity of transformed proteins. W represents the leaf protein extract from wild type, that is nontransgenic plant, 1–3 and 6–8 represents the leaf protein extract from wild type, that is untransformed plant. The transparent region indicates the presence of trypsin inhibitor activity. The inhibiting activities expressed by transformants 1, 2 and 8 are strongest.
Figure 5:
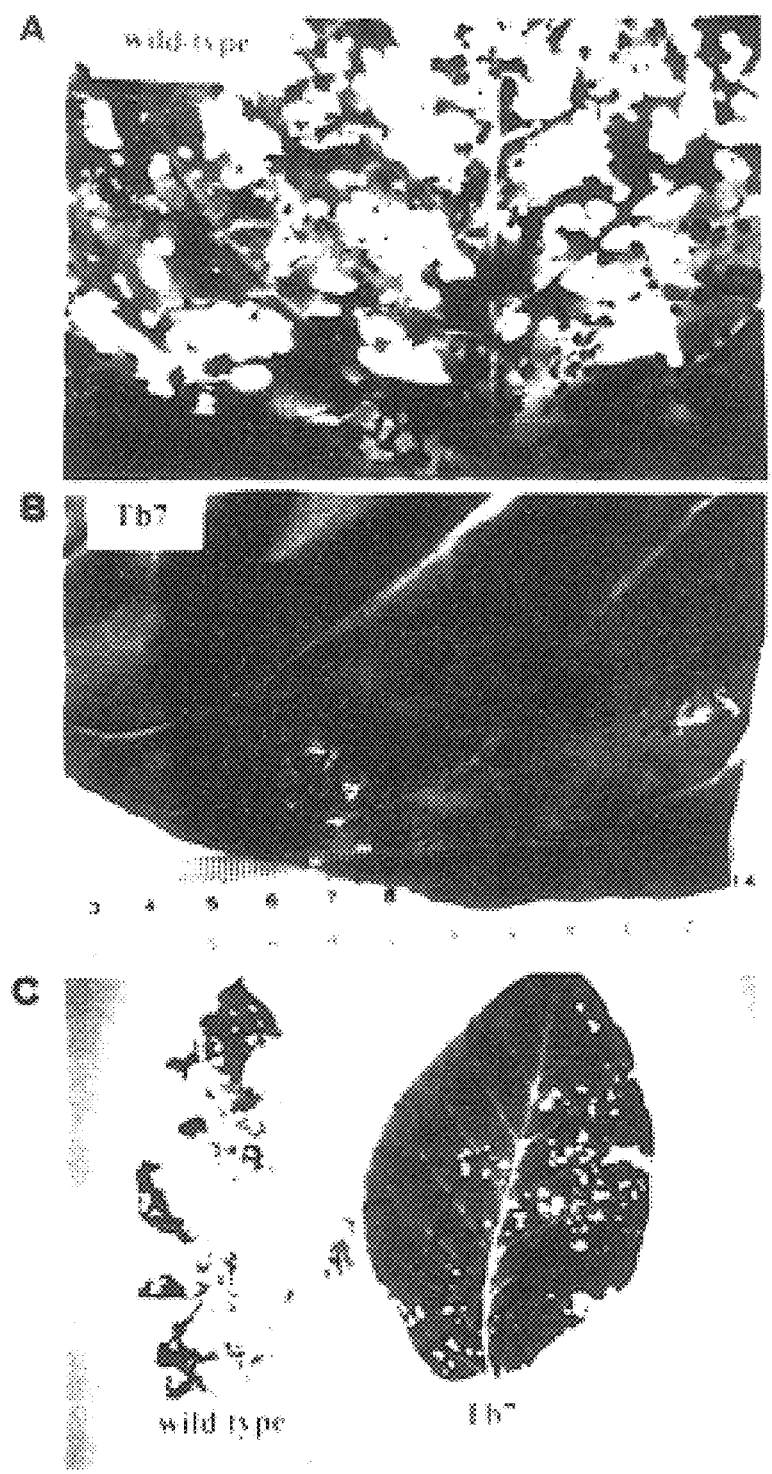
FIG. 5 The bitten conditions by *Spodoptera litura* (tobacco cutworm) in the insect-resistance test.

According to the present invention, a transformation vector TIA::pBI 121 was prepared. The plasmid construct of pBI 121 is shown in FIG. 2. It was cut at the XbaI/BamHI site in pBI 121, and a sporamin gene was inserted into that site.

According to the present invention, a transformant bacterium was prepared by direct transformation of TIA::pBI 121 into *Agrobacterium tumefaciens* LBA 4404. Because vector pBI 121 carries neomycin transferase gene, so by using Kanamycin the successfully transformed Agrobacteria or leaves may be selected. Among which a representative transformant *Agrobacterium tumefaciens* tBA has been deposited in Research Institute of Food Industrial Development at the date of Jan. 27, 1997 under accession number of CCRC 910072.

The following examples are for further illustration of the present invention, and are not intended to limit the scopes of the present invention.

EXAMPLE 1

The Construction of Vectors in which Sweet Potato Sporamin Gene was Inserted A full-length cDNA sequence of sweet potato sporamin gene, which was isolated by the inventors from a sweet potato tuberous cDNA library, and has been submitted to GenBank under accession number U17333, designated spTi-1 was used (Chen, 1994). This cDNA fragment was subcloned at a XbaI/BamHI site into the binary vector pBI 121 (Clonetech™ Co.) under the control of 35S CaMV promoter, and with the 3'-Nos terminator. Using standard molecular procedure, the sequence of the construct was determined to identify the precise orientation (Sambrook et al., Molecular Cloning: A Laboratory Manual, Cold Spring Harbor Laboratory Press., 1989). The construct of that vector is shown in FIG. 2, and designated TIA::pBI 121.

The direct transformation of the vector obtained as described above into *Agrobacterium tumefaciens* LBA 4404 (Höfgen & Willmitzer, Nucleic Acids Research Vol. 16, pp. 9877–9878, 1988) offered ten transformants, L1 to L10. One of the representative transformants is tBA, which has been deposited in Research Institute of Food Industrial Development. The integrity of the plasmid was verified by Southern blot hybridization analysis. The results are shown in FIG. 3, from which it may be demonstrated that a sporamin gene has been transformed into *Agrobacterium tumefaciens* LBA 4404.

EXAMPLE 2

Tobacco Leaf-disc Transformation

A *A. tumefaciens*-mediated gene transfection of a sporamin gene into tobacco (*Nicotiana tabaccum* cv. W38) was used, following the method of Horsch et al. (Horsch et al., Science Vol. 227, pp. 1229–1231, 1985). The *A. tumefaciens* culture obtained from Example 1, which contains a sporamin gene insert, was incubated with tobacco leaf discs for 3 days in the dark at 28° C. After rinsing with sterile water several times, leaf discs were subsequently cultured in petri dishes containing Kanamycin at 28° C., 16 h light for the selection of successfully transformed regenerating seedling. After 2 to 3 weeks, shoots were excised and transferred to another medium for root-induction. Three to four week-old plantlets were transferred to pots, and grown in a controlled environment growth chamber, 28±2° C., 16 h light/day, 75% relative humidity. The expression of TIA gene and the production of protein with trypsin inhibitor activity by transformants were determined by Western blot analysis.

EXAMPLE 3

Assay for Inhibitor Activity

The trypsin inhibitor activity of transgenic tobacco protein was determined. The protein electrophoresis of protein extracts from transgenic tobacco leaves was carried out on SDS-PAGE, then an appropriate trypsin solution was added. After incubation at room temperature for 30–40 minutes, the excess trypsin was removed by rinsing, trypsin substrate (N-acetyl-DL-phenylalanine E-naphthyl ester (APNE)) solution and dye solution (O-dianisidine, tetrazoitize solution) were added, and the gel was incubated at room temperature for 2–12 hours. The reaction was stopped by adding acetic acid. The electrophoresis film was examined for the presence of any transparent region that resulted from the existence of trypsin inhibitor and unreaction of trypsin and substrate so that the gel cannot be stained. Therefore, the transparent region indicates the presence of trypsin inhibitor activity. The results were shown in FIG. 4.

EXAMPLE 4

Test for Insect-resistance of Tobacco Transformants

Early second instar larvae of *Spodoptera litura* (tobacco cutworm) were used, and fed with sporamin gene-transformed tobacco leaves individually, incubated in a growth chamber (set at temperature of 25±1° C.,70±5% relative humidity), and the mortality of larvae, the average body weight of survival larvae, and the ratio of leaf area eaten by larvae were recorded. Each treatment was carried out with 30 larvae, and untransformed tobacco clone was used as Control. The result is listed in Table 1. In comparison with Control, the transgenic plant can cause the death of larvae. In particular for Tb 7 plant, the survival rate of larvae is only 6.7%, and the average weight of survival larvae is ⅕ of that recorded in Control. The comparison in bitten leaf area of wild tobacco (Control) and sporamin gene-transformed tobacco (Tb 7) is also provided, as shown in FIG. 5. From the integrity of leaves of Tb 7 plant, it suggested that sporamin gene-transformed plants exhibit better resistance for *Spodoptera litura* (tobacco cutworm).

TABLE 1

Result of insect-resistance test in transgenic tobacco

| | % Insect Survival | Average Body Weight (mg) | Leaf Area Eaten/lar. ($cm^2$) |
|---|---|---|---|
| Wild type | 100.0 | 33.4 ± 4.4 | 5.5 |
| Tb-l | 43.5 | 15.7 ± 4.2 | 4.3 |
| Tb-2 | 77.8 | 17.8 ± 5.9 | 2.6 |
| Tb-3 | 96.4 | 12.0 ± 3.1 | 1.6 |
| Tb-6 | 96.8 | 24.6 ± 1.8 | 6.4 |
| Tb-7 | 6.7 | 6.1 ± 0.8 | 0.8 |
| Tb-8 | 91.3 | 16.3 ± 3.3 | 2.2 |

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 899 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 56..712

(ix) FEATURE:
      (A) NAME/KEY: polyA_site
      (B) LOCATION: one-of(796, 842, 856)

(xi) SEQUENCE DESCRIPTION: SEQ ID NO:1:

```
AATTAAACAT CATTACCTCT TCGCTTTCTC CCAATTAAGG TTGTCATCTG CCACC ATG        58
                                                              Met
                                                               1

AAA GCC CTC ACA CTG GCA CTC TTC TTA GCC CTT TCC CTC TAT CTC CTC        106
Lys Ala Leu Thr Leu Ala Leu Phe Leu Ala Leu Ser Leu Tyr Leu Leu
             5                  10                  15

CCC AAT CCC GCC CAT TCC AGG TTC AAT CCC ATC CGC CTC CCC ACC ACA        154
Pro Asn Pro Ala His Ser Arg Phe Asn Pro Ile Arg Leu Pro Thr Thr
         20                  25                  30

CAC GAA CCC GCC TCC TCT GAA ACT CCA GTA CTG GAC ATC AAC GGC GAC        202
His Glu Pro Ala Ser Ser Glu Thr Pro Val Leu Asp Ile Asn Gly Asp
     35                  40                  45

GAG GTC CGC GCC GGC GGG AAC TAC TAC ATG GTC TCC GCC ATA TGG GGA        250
Glu Val Arg Ala Gly Gly Asn Tyr Tyr Met Val Ser Ala Ile Trp Gly
 50                  55                  60                  65

GCC GGC GGG GGA GGG CTA AGA CTC GCC CAC TTG GAC ATG ATG TCC AAA        298
Ala Gly Gly Gly Gly Leu Arg Leu Ala His Leu Asp Met Met Ser Lys
                 70                  75                  80

TGC GCC AGC GAC GTC ATC GTA TCC CCC AAC GAC TTA GAC AAC GGC GAC        346
Cys Ala Ser Asp Val Ile Val Ser Pro Asn Asp Leu Asp Asn Gly Asp
                     85                  90                  95

CCC ATC ACC ATC ACG CCG GCG ACG GCC GAC CCG GAA TCC ACC GTG GTC        394
Pro Ile Thr Ile Thr Pro Ala Thr Ala Asp Pro Glu Ser Thr Val Val
                100                 105                 110

ATG GCG TCG ACG TAC CAG ACT TTC CGG TTC AAC ATC GCC ACC AAC AAG        442
Met Ala Ser Thr Tyr Gln Thr Phe Arg Phe Asn Ile Ala Thr Asn Lys
            115                 120                 125

CTC TGC GTG AAC AAC GTG AAC TGG GGA ATC CAG CAC GAC AGC GCG TCC        490
Leu Cys Val Asn Asn Val Asn Trp Gly Ile Gln His Asp Ser Ala Ser
130                 135                 140                 145

GGG CAG TAT TTC CTG AAA GCC GGC GAG TTT GTG TCC GAC AAT AGC AAC        538
Gly Gln Tyr Phe Leu Lys Ala Gly Glu Phe Val Ser Asp Asn Ser Asn
                150                 155                 160

CAG TTC AAG ATT GAG CTG GTG GAT GCC AAC CTT AAC TCC TAC AAA CTC        586
Gln Phe Lys Ile Glu Leu Val Asp Ala Asn Leu Asn Ser Tyr Lys Leu
            165                 170                 175

ACT TAC TGT CAG TTC GGC TCC GAT AAA TGC TAC AAC GTC GGC AGA TTC        634
Thr Tyr Cys Gln Phe Gly Ser Asp Lys Cys Tyr Asn Val Gly Arg Phe
        180                 185                 190
```

```
CAC GAC CAC ATG TTG AGG ACC ACG CGT TTG GCT CTC TCC AAT TCT CCC          682
His Asp His Met Leu Arg Thr Thr Arg Leu Ala Leu Ser Asn Ser Pro
    195                 200                 205

TTC GTT TTT GTC ATC AAA CCT ACC GAT GTG TAATGTAACA CTGAAAAGCG            732
Phe Val Phe Val Ile Lys Pro Thr Asp Val
210                 215

CCGGTTATGA GGTTGCATGG TAGCTATGCA ACGTTGCCAC TTTGACAACG TTGTACGTGT        792

AAGAATAAAC ATGCAACAAA TCCGAGCTGG TATGGTTGTG TAAATCCTAA ATAAATCCGA        852

AGAAATAATA AGGATAAAAT ATTATCCTGT GTTTGTTTTA ATTCTCC                      899

(2) INFORMATION FOR SEQ ID NO:2:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Ala Leu Thr Leu Ala Leu Phe Leu Ala Leu Ser Leu Tyr Leu
1               5                   10                  15

Leu Pro Asn Pro Ala His Ser Arg Phe Asn Pro Ile Arg Leu Pro Thr
                20                  25                  30

Thr His Glu Pro Ala Ser Ser Glu Thr Pro Val Leu Asp Ile Asn Gly
            35                  40                  45

Asp Glu Val Arg Ala Gly Gly Asn Tyr Tyr Met Val Ser Ala Ile Trp
        50                  55                  60

Gly Ala Gly Gly Gly Leu Arg Leu Ala His Leu Asp Met Met Ser
65                  70                  75                  80

Lys Cys Ala Ser Asp Val Ile Val Ser Pro Asn Asp Leu Asp Asn Gly
                85                  90                  95

Asp Pro Ile Thr Ile Thr Pro Ala Thr Ala Asp Pro Glu Ser Thr Val
                100                 105                 110

Val Met Ala Ser Thr Tyr Gln Thr Phe Arg Phe Asn Ile Ala Thr Asn
            115                 120                 125

Lys Leu Cys Val Asn Asn Val Asn Trp Gly Ile Gln His Asp Ser Ala
        130                 135                 140

Ser Gly Gln Tyr Phe Leu Lys Ala Gly Glu Phe Val Ser Asp Asn Ser
145                 150                 155                 160

Asn Gln Phe Lys Ile Glu Leu Val Asp Ala Asn Leu Asn Ser Tyr Lys
                165                 170                 175

Leu Thr Tyr Cys Gln Phe Gly Ser Asp Lys Cys Tyr Asn Val Gly Arg
            180                 185                 190

Phe His Asp His Met Leu Arg Thr Thr Arg Leu Ala Leu Ser Asn Ser
        195                 200                 205

Pro Phe Val Phe Val Ile Lys Pro Thr Asp Val
        210                 215
```

What we claim is:

1. A sporamin gene isolated from sweet potato consisting of the following nucleotide sequence (SEQ ID NO:1):

```
1    AATTAAACAT CATTACCTCT TCGCTTTCTC CCAATTAAGG
```
```
     TTGTCATCTG
51   CCACCATGAA AGCCCTCACA CTGGCACTCT TCTTAGCCCT
65   TTCCCTCTAT
```

-continued

```
101  CTCCTCCCCA ATCCCGCCCA TTCCAGGTTC AATCCCATCC
     GCCTCCCCAC

151  CACACACGAA CCCGCCTCCT CTGAAACTCC AGTACTGGAC
     ATCAACGGCG

201  ACGAGGTCCG CGCCGGCGGG AACTACTACA TGGTCTCCGC
     CATATGGGGA

251  GCCGGCGGGG GAGGGCTAAG ACTCGCCCAC TTGGACATGA
     TGTCCAAATG

301  CGCCAGCGAC GTCATCGTAT CCCCCAACGA CTTAGACAAC
     GGCGACCCCA

351  TCACCATCAC GCCGGCGACG GCCGACCCGG AATCCACCGT
     GGTCATGGCG

401  TCGACGTACC AGACTTTCCG GTTCAACATC GCCACCAACA
     AGCTCTGCGT

451  GAACAACGTG AACTGGGGAA TCCAGCACGA CAGCGCGTCC
     GGGCAGTATT

501  TCCTGAAAGC CGGCGAGTTT GTGTCCGACA ATAGCAACCA
     GTTCAAGATT

551  GAGCTGGTGG ATGCCAAGGT TAAGTCCTAC AAACTCACTT
     ACTGTCAGTT

601  CGGCTCCGAT AAATGCTACA ACGTCGGCAG ATTCCACGAC
     CACATGTTGA

651  GGACCACGCG TTTGGCTCTC TCCAATTCTC CCTTCGTTTT
     TGTCATCAAA

701  CCTACCGATG TGTAATGTAA CACTGAAAAG CGCCGGTTAT
     TGTCATCAAA
```

-continued

```
751  GGTAGCTATG CAACGTTGCC ACTTTGACAA CGTTGTACGT
     GTAAGAATAA

801  ACATGCAACA AATCCGAGCT GGTATGGTTG TGTAAATCCT
     AAATAAATCC

851  GAAGAAATAA TAAGGATAAA ATATTATCCT GTGTTTGTTT
     TAATTCTCC.
```

2. A binary transformation vector comprising the sporamin gene according to claim 1.

3. The transformation vector according to claim 2, which is pBI 121.

4. A transformed bacterium comprising the transformation vector according to claim 2.

5. The transformed bacterium according to claim 4, which is *Agrobacterium tumefaciens*.

6. A method of controlling pests, which comprises transforming the sporamin gene according to claim 1 into a plant to enhance the insect resistance of the plant.

7. The method according to claim 6, in which the sporamin gene is transformed into the plant via a bacterium transformed with the sporamin gene.

8. The method according to claim 7, in which the bacterium is transformed with the sporamin gene via a binary vector comprising the sporamin gene.

9. The method according to claim 8, in which the binary vector is pBI 121.

10. The method according to claim 7, in which the bacterium for transforming the sporamin gene into plants is *Agrobacterium tumefaciens*.

\* \* \* \* \*